United States Patent [19]
Mericle

[11] Patent Number: 4,595,007
[45] Date of Patent: Jun. 17, 1986

[54] SPLIT RING TYPE TISSUE FASTENER

[75] Inventor: Robert W. Mericle, Lebanon, N.J.

[73] Assignee: Ethicon, Inc., Somerville, N.J.

[21] Appl. No.: 475,267

[22] Filed: Mar. 14, 1983

[51] Int. Cl.⁴ .................. A61B 17/00; A61B 17/08
[52] U.S. Cl. .......................... 128/334 R; 128/335; 128/335.5; 63/12; 63/14 G
[58] Field of Search .............. 24/67.9; 63/12, 14 G; 128/305, 92 B, 92 BB, 335, 335.5, 326, 337; 227/108

[56] References Cited

U.S. PATENT DOCUMENTS

| | | | |
|---|---|---|---|
| 67,545 | 8/1867 | Hodgins | 128/340 |
| 2,514,047 | 7/1950 | Goforth | 24/67.9 |
| 3,683,891 | 8/1972 | Eskridge et al. | 128/305 |
| 3,858,783 | 1/1975 | Kapitanov et al. | 227/108 |
| 4,011,873 | 3/1977 | Hoffmeister | 128/326 |
| 4,214,456 | 7/1980 | Hannum | 63/12 |

FOREIGN PATENT DOCUMENTS

| | | | |
|---|---|---|---|
| 855438 | 11/1970 | Canada | 63/12 |
| 1712 | of 1885 | United Kingdom | 63/12 |
| 596232 | 2/1978 | U.S.S.R. | 128/69 |
| 652940 | 3/1979 | U.S.S.R. | 128/92 B |
| 915844 | 3/1982 | U.S.S.R. | 128/92 BB |

OTHER PUBLICATIONS

Ethicon, Inc., "Manual of Operative Procedures", 10th ed., 1981, p. 7, from Examiner's copy.

Primary Examiner—Gene Mancene
Assistant Examiner—C. W. Shedd
Attorney, Agent, or Firm—Robert L. Minier

[57] ABSTRACT

A sterile, surgical, unitary fastener having a generally circular shape and with its free ends disposed laterally with respect to each other. Methods and instruments for forming and placing such fasteners to join tissue together.

2 Claims, 8 Drawing Figures

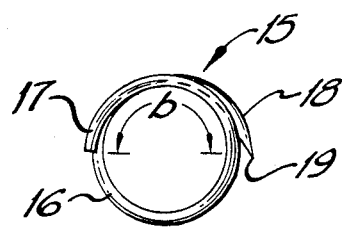
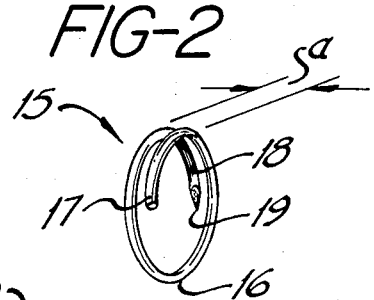
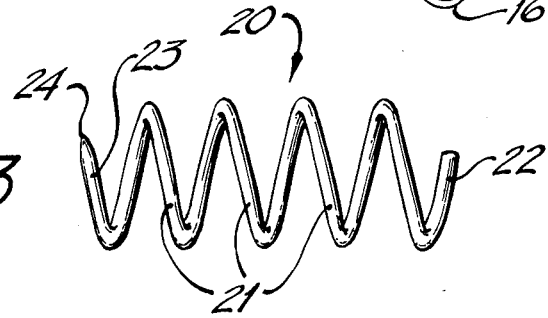
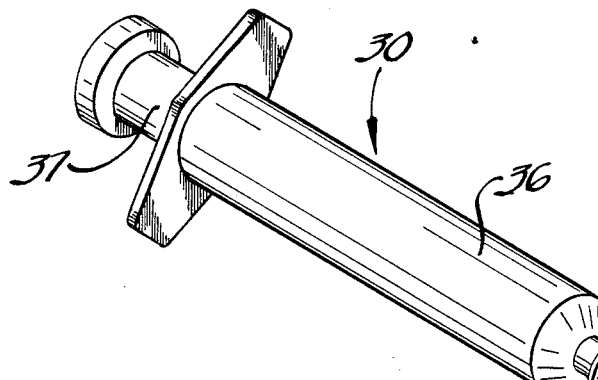
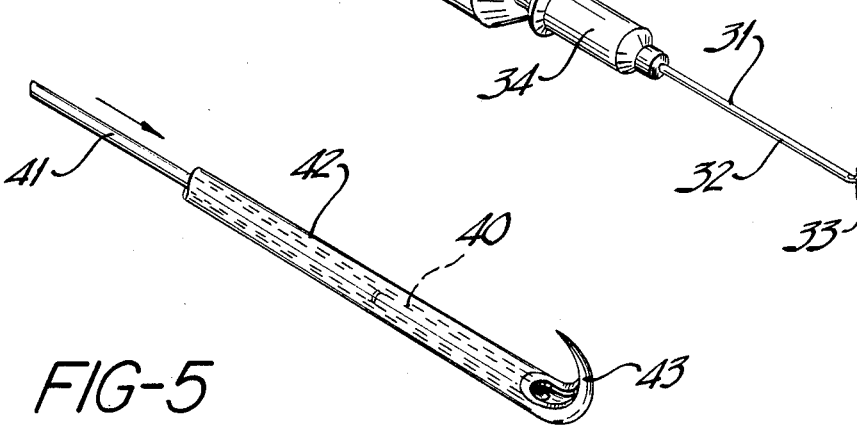

SPLIT RING TYPE TISSUE FASTENER

BACKGROUND OF THE INVENTION

The present invention relates to means for joining tissue together and medical instruments for applying such means.

The joining of tissue is of critical importance in medical and surgical treatments. The tissues joined may be those of fascia, various organs, muscle, skin and the like. In the past, tissues have been joined by using various types of sutures with specific sutures being developed for the joining of various specific tissues. More recently, metallic fasteners have been developed. For example, staples for the joining of skin. Also, staples and appropriate instruments have been developed for joining tissues including those of the intestine and other organs. Recently, work has been done on trying to develop nonmetallic fasteners for tissues and to make these fasteners from either absorbable or non-absorbable polymeric materials. Patents which describe various types of such fasteners are U.S. Pat. Nos. 4,006,747 and 4,060,089.

In U.S. Pat. No. 3,545,444 there is disclosed a wire suture wrapping instrument which describes a wire suture which coils upon itself and may be placed about a tubular member to clamp that tubular member. The wire is wound around itself to the desired degree to obtain the desired tightness. A related instrument is described in U.S. Pat. No. 3,735,762.

Though the above-described fasteners are satisfactory for many different end uses, there has not been developed a single configured fastener that can be used with virtually any tissue, whether skin, fascia, muscle, organ, or the like. In order to have a suitable fastener that can be used in all end uses, it must provide hemostatis without necrosis; that is, it must hold the tissue together and stop bleeding without killing tissue. The fastener should be usable with a wide variety of tissues; i.e., tissue of various thickness as well as tissue of various strength. The fastener should be simple to place and be placeable with consistency. Each fastener should be placed in the same manner providing the same degree of tension in closing as other fasteners. Furthermore, the fastener should be simple and economical to manufacture.

What I have discovered is a new type of fastener which may be used on various types of tissues. The fastener is simple in construction and economical to manufacture. The fastener is easy to place and each fastener can be placed in a consistent manner because of its simple design. My new fastener will hold various types of tissue and tissue configurations together preventing blood loss and providing hemostasis without causing undue trauma or necrosis.

SUMMARY OF THE PRESENT INVENTION

The fastener of the present invention is of unitary construction and may be used to join animal or human tissue. The fastener has a generally cylindrical shape with a pair of free ends. The free ends of the fastener are disposed laterally to form a split ring. In certain embodiments of the present invention, the fastener may comprise a plurality of cylindrical shapes joined together in a continuous mode and with the free ends spaced laterally from one another. In other embodiments of the present invention the free ends of the fastener may abut one another but are laterally disposed with respect to one another.

My new fastener may be applied by various types of instruments. The fastener may start as a relatively straight piece of material preferably sharpened to a very fine point at one end. The applying instrument has a curved forming member and a driver. The free end of the curved formed member is offset from the other or driving end attached to the instrument and driver. The straight fastener is driven by the driver through the curved forming member to the free end so that the sharpened point of the fastener is immediately adjacent the tissue to be joined. As the member is curved, it is directed so the pointed end engages the tissue to be joined. The member is continued to be driven in a circular configuration through the tissue. As the member is curved back on itself to form a ring or loop, the tissue that has been engaged is brought together. This action may be accomplished a number of times to form plural segmented loops engaging the tissue. In certain embodiments, the instrument itself may have a sharpened end which may be used to approximate the tissue to be joined and the fastener then formed as described.

BRIEF DESCRIPTION OF THE DRAWINGS

FIG. 1 is a side view of a new unitary fastener of the present invention;

FIG. 2 is a view in perspective of the fastener of FIG. 1;

FIG. 3 is a front view of another embodiment of the unitary fastener of the present invention;

FIG. 4 is a view in perspective showing one type of instrument for applying the fasteners of the present invenion;

FIG. 5 is an enlarged close-up view in perspective of the forming end of the instrument depicted in FIG. 4;

DETAILED DESCRIPTION OF THE DRAWINGS

Figure 6:
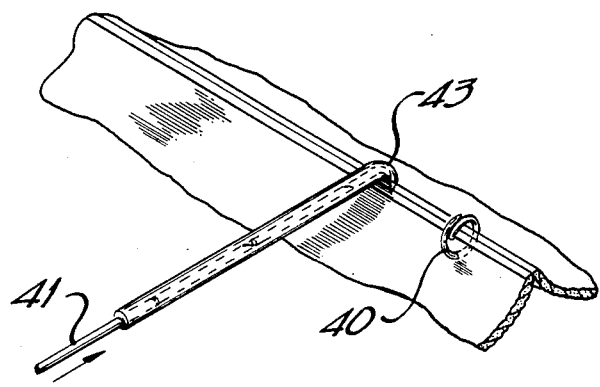
FIG. 6 is a view in perspective showing the forming end depicted in FIG. 5 in a position to place a fastener into tissue.

Referring to the drawings, in FIG. 1 there is shown a single loop forming the unitary fastener 15 of the present invention. The body 16 of the loop is circular in shape and as more clearly shown in FIG. 2 the free ends 17 and 18 of the fastener are spaced laterally from one another. The spacing of the free ends of the loop may be varied as to lateral offset (a) and overlap (b). The general configuration of the loop may also be varied; i.e., circular, oval, ellipsoidal, etc. One end 19 of the fastener is sharpened to a fine point to aid in tissue penetration.

In FIG. 3 there is shown another embodiment of the fastener of the present invention. The fastener 20 comprises a plurality of loops 21 which are continuous and with the free ends 22 and 23 spaced laterally from one another. One of the free ends of the fastener is sharpened to a fine point 24 to aid tissue penetration. To use this fastener, the pointed end 24 of the fastener is inserted through one side of the tissue to be joined. This action is continued a plurality of times causing the fastener as it passes through the tissue to join the tissue along a longitudinal line.

An instrument for applying the fasteners of the present invention is depicted in FIG. 4. In this embodiment the instrument 30 has a configuration similar to that of a hypodermic syringe with an applying head 31 in the form of an elongated member 32 having a curved end 33. The instrument includes an area for carrying a plurality of unformed fasteners 34 of the present invention. The unformed fasteners have a straight configuration preferably with a pointed end. The hypodermic body 36 includes an appropriate pusher 37 which through an appropriate driver (not shown) will push one of the straight fasteners down the elongated head. This is more clearly depicted in FIG. 5 which is an enlarged view of the head of the applying instrument depicted FIG. 4. If the hypodermic-type instrument is meant to carry a plurality of fasteners, it selects a fastener 40, which is in a straight configuration, from the carrying area and a driver 41 pushed by the hypodermic plunger pushes the straight fastener down the hollow tube head 42 to the curved open tip 43. The end of the tip 43 is slightly offset laterally from the longitudinal axis of the hollow tube head 42. This offset causes the pointed end of the fastener to be offset or laterally spaced from the trailing end as the fastener is placed. As more clearly shown in FIG. 6, the curved tip 43 is placed adjacent the tissue 44 to be joined with the tissue approximated. The pusher continues to force the fastener out the curved tip through the tissue curving the member as it passes through the tissue.

Figure 7:
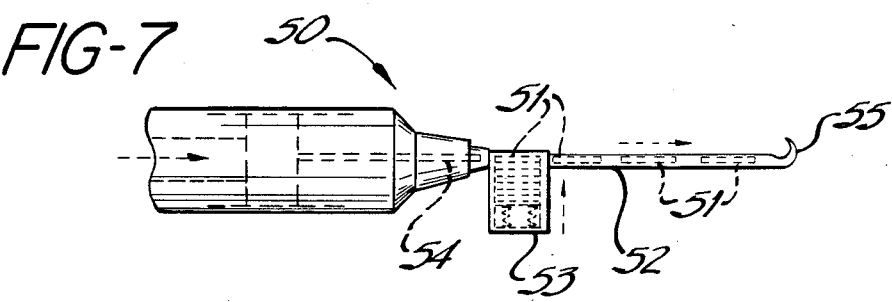
FIG. 7 is a cross-sectional view of another type of instrument which may be used to apply the unitary fasteners of the present invention.

In FIG. 7 there is shown a cross-sectional view of a portion of an instrument showing one technique for providing for a plurality of fasteners to be disposed one after the other in a suitable forming head. In this embodiment, the hypodermic type instrument 50 is used and a plurality of unformed fasteners 51 is provided to the hollow tube applying head 52 through a spring loaded magazine 53. The driver 54 pushes fasteners down the hollow tube to the curved pointed open head 55. The driver places the front fastener and is withdrawn to accept another straight fastener in the line.

It should be appreciated that on placing the fasteners, once the fastener is curved to some minimum curvature, on continuing to push the fastener it will continue to follow that curvature; hence, you only need to curve the fastener from about 10° to 100° C. with the appropriate instrument head and the fastener will continue to follow the desired curvature. The tightness of the curvature will depend on the radius of curvature at the forming head of the instrument and the sideways offset by the tip angle.

Figure 8:
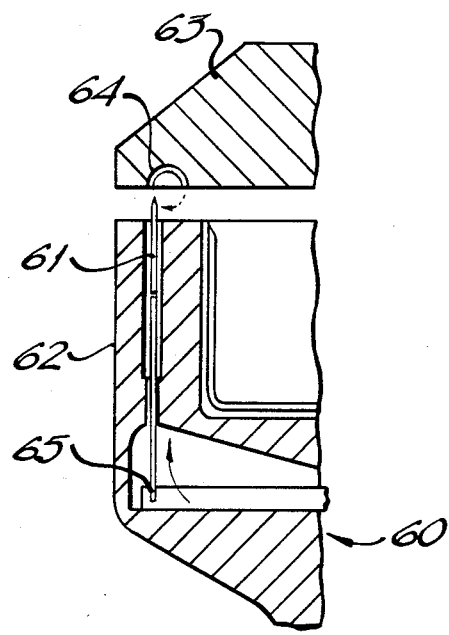
FIG. 8 is a cross-sectional view of the portion of a very specific type of instrument which may be used to apply the fasteners of the present invention to intestinal tissue.

FIG. 8 shows a cross-sectional view of a specific type of instrument which is a intraluminal stapling device 60 and depicts the manner in which my new fastener may be used with such a device. The straight unformed fastener 61 is held in one end 62 of the intraluminal stapler and the opposite end 63 of the intraluminal stapler carries a curved anvil 64. The tissue to be joined is placed between the two instrument ends 62 and 63 as is normally the case. A pusher 65 pushes the straight fastener through the tissue to be joined and against the circular anvil causing the straight piece to form a loop in accordance with the present invention and join the tissue.

As may be appreciated, the size of the loop may be varied over wide ranges depending upon the tissue that is desired to be joined. Furthermore, the diameter of the fastener may be varied over wide ranges again depending on the tissue it is desired to join.

It is preferred that the fasteners of the present invention be made from metallic material such as stainless steel, tantalum, titanium, and the like though in certain instances if the plastic material is flexible enough so that it can be formed into a circular shape and maintain that circular shape, plastic materials may also be used. Biologically absorbable materials may also be considered for use in making the fasteners of the present invention.

The surgical fasteners of the present invention must be sterilized. The metallic fasteners of the present invention may be sterilized by heat, radiation, ethylene oxide, or the like.

The instruments used in placing the fasteners of the present invention may either place a single fastener or may place multiple fasteners. The instruments may be reusable; that is, they may accept cartridges of the fasteners and the instrument itself reusable or the instrument itself may be totally disposable as is the case with various types of surgical staplers.

Having now described the present invention and the manner in which it may be carried out, it should be appreciated that various modifications may be made without departing from the spirit and scope of the present invention.

What is claimed is:

1. A method for joining tissue comprising approximating the tissue to be joined, inserting one end of a fastener through the approximated tissue, said fastener being formable into a given shape and capable of maintaining such shape once it has been formed, bending said fastener into a generally circular shape while said fastener is being inserted through the tissue, and simultaneously disposing said inserted end of said fastener laterally from the opposite end of said fastener while said fastener is being bent, whereby the tissue is joined by the maintained shape of the fastener.

2. A method according to claim 1 wherein the fastener is continually bent to form a plurality of connected generally circular shapes.

* * * * *